United States Patent [19]

Dzemeshkevich et al.

[11] Patent Number: 4,692,164
[45] Date of Patent: Sep. 8, 1987

[54] BIOPROSTHETIC HEART VALVE, METHODS AND DEVICE FOR PREPARATION THEREOF

[75] Inventors: Sergei L. Dzemeshkevich, Moscow; Nikolai N. Zavalishin, Moskovskaya; Svetlana M. Krasovskaya, Moscow; Valery M. Sagalevich, Moscow; Boris A. Konstantinov, Moscow; Alexandr K. Nenjukov, Moscow; Alexei S. Ivanov, Moscow, all of U.S.S.R.

[73] Assignee: Moskovskoe Vysshee Tekhnicheskoe Uchilische, Imeni N.E. Baumana, Moscow, U.S.S.R.

[21] Appl. No.: 837,094

[22] Filed: Mar. 6, 1986

[51] Int. Cl.⁴ .......................... A61F 2/24; A61F 2/76; A61B 17/00
[52] U.S. Cl. .................................. 623/2; 128/303 R; 623/900
[58] Field of Search ................ 623/2, 900; 128/303 R

[56] References Cited

U.S. PATENT DOCUMENTS

| | | | |
|---|---|---|---|
| 3,744,060 | 7/1973 | Bellhouse et al. | 623/2 |
| 3,755,823 | 9/1973 | Hancock | 623/900 X |
| 4,035,849 | 7/1977 | Angell et al. | 623/2 |
| 4,106,129 | 8/1978 | Carpentier et al. | 623/2 |
| 4,218,782 | 8/1980 | Rygg | 623/2 |
| 4,247,292 | 1/1981 | Angell | 623/2 |
| 4,624,822 | 11/1986 | Arru et al. | 623/2 X |

FOREIGN PATENT DOCUMENTS 2399832 3/1979 France ..................... 623/2

Primary Examiner—Ronald L. Frinks
Attorney, Agent, or Firm—Burgess, Ryan and Wayne

[57] ABSTRACT

A bioprosthetic heart valve comprising a biological transplant on a frame consisting of a supporting ring with struts extending therefrom over a toroidal surface and connected with said ring by arcuate portions of an additional ring, a covering made from a biologically inert material with an isolation spacer, which form a toroidal envelope, the biological transplant secured to the covered-up frame having envelopes shaped like aortic sinuses, joining smoothly the cusps whose number corresponds to the number of envelopes; a method of preparing the biological transplant from the aortic valve of an animal or human being comprising the dissection of the aortic root with aortic valve and cutting out a transplant with cusps, fibrous ring and aortic sinuses from a flap of biological tissue with the aid of a device comprising a punch and two matrix plates, said punch being made in the form of a plate with projections and bulges thereon, entering the cutouts on the matrix plates, and a method for preparing the biological transplant from a flap of biological tissue with the aid of said device comprising simultaneous forming of cusps and envelopes smoothly mating therewith and suturing them up along the conjugate line through a reinforcing spacer. A method of preparing the bioprosthetic heart valve comprising the suturing of the biological transplant to the supporting and additional frame rings through the upper and lower edges of envelopes shaped like aortic sinuses.

11 Claims, 18 Drawing Figures

BIOPROSTHETIC HEART VALVE, METHODS AND DEVICE FOR PREPARATION THEREOF

FIELD OF THE ART

The present invention relates to the field of medicine and, more specifically, to cardiosurgery, particularly to the bioprosthetic heart valve, the methods and devices for its preparation.

The bioprosthetic heart valve is intended for surgical treatment of acquired and congenital heart diseases involving replacement of affected cardiac valves. In such a replacement the object is to recover the lost valvular function which consists in hermetic closing of the valve orifice and passing the blood flow without sizable hydraulic resistance at the corresponding phases of the heart cycle while retaining the natural characteristics of the flow. Besides, the prosthesis should be athrombogenic, cause no blood hemolysis, have a minimum weight and size, produce no noise in operation, etc. Thus, the basic requirements for the prosthesis are perfect hydraulic characteristics and a minimum mechanical and biological effect on the passing blood. Recovery of the lost valvular function in any one of the four heart valves will normalize the hemodynamic parameters and the functioning of the heart as a whole.

An acute problem in medicine today is surgical treatment of acquired and, particularly, congenital heart valve diseases combined with other heart troubles causing a sharp deterioration of the central hemodynamics and, as a consequence, serious illnesses and fatal outcome. As surgical experience in replacement of affected heart valves by prostheses is gradually accumulated, the more obvious becomes the fact that a further improvement of the long-term results of prosthetics can be attained only by perfecting the functional characteristics of the prostheses proper.

All the currently used prostheses of heart valves can be classified into artificial (with an inertia closing element and petal-type) and biological (prepared from the aortic valve of an animal or a flap of biological tissue). The category of valves with inertia closing element includes, for example, ball and disc type valves. They consist, essentially, of a circular seat with arcuate portions which limit the movement of the closing element and hold it in the valve seat. The closing element of the ball valve comprises a ball of a hemocompatible wear-resistant material whose centre of gravity coincides with the axis of the valve lumen. The closing element of the disc valve is made in the form of a disc from a hemocompatible wear-resistant material whose centre of gravity is located eccentrically with relation to the limiting arcuate portions (arches). The disc may be flat, convexo-concave or biconvex.

The valves with inertia closing elements are opened and closed by the pressure differential which builds up a force moving the ball-type closing element or a moment which overturns the disc-type closing element. In the open valve the closing element is held in position by the pressure differential applied to it and by the force of the velocity head of the blood flow passing through the valve.

However, the blood flow past the closing element and limiting arcuate portions disturbs the central nature of the flow thereby worsening its hemodynamic characteristics. Behind the closing element there arise congested and abrupt zones with considerable shear stresses which destroy the formed elements of blood. At the moment of valve closing and opening the closing element strikes the limiting arcuate portions and the seat, which also injures the formed blood elements and conduces to formation of thrombi on the valve. To reduce the risk of thromboembolic complications the patients with an artificial ball or disc-type valve require lifelong administration of anticoagulants and regular control of their coagulating system. This hampers and often eliminates the possibility of surgical treatment of elderly patients with whom the risk of thromboembolic complications grows with age; of patients residing in rural regions and children with whom control of administration of anticoagulants involves certain difficulties; or patients intolerant to anticoagulants; and of patients suffering from disturbances of the blood coagulating system. In view of substantial differences in the inertia of the closing element and the acting blood column, a phenomenon of hydraulic shock develops in the space after the valve. This, together with a large weight of the valve imposes additional loads on the myocardium of the patient. The impact nature of interaction between the closing element with the limiting arcuate portions and the seat brings about a considerable cardiac murmur caused by the functioning of the valve and thus creating a negative psychoemotional effect on the patient.

Known in the art is a disc-type prosthesis of the cardiac valve (cf. FRG Patent No. 2640246, Cl. A61F 1/22, 1977) made as a saddle with limiting arcuate members excentrically extending into the inner cavity thereof, with a convexo-concave disc disposed between said arcuate members in such a manner that a small gap is provided between said disc and the saddle of the valve.

The prosthesis operates as follows. As the prosthesis opens upon increase of pressure at the concave side of the disc, insofar as the centre of gravity of the disc has an excentricity in relation to the limiting arcuate members, the disc turns over and slides between said members, making, when in the open position, an angle of 50° to 80° with the plane of the ring and dividing the blood stream passing through the prosthesis into two unequal portions.

In addition to all the disadvantages common to the prostheses of cardiac valves with inertia closing members, the disc-type prosthesis of the cardiac valve is also noted for an appreciable regurgitation, i.e. a reverse blood flow through the valve, associated with the origination of a back pressure differential required for closing the prosthesis, and with the provision of a positive gap between the disc and the saddle of the prosthesis.

Artificial petal-type prostheses of the cardiac valves are made in the form of a body with shape-sustaining cusps of synthetic materials attached thereto. These prostheses function as follows. As a pressure differential is built up on the prosthesis cusps, they lose their stability and are flexed in the zone of attachment to the body while their free edges move in the direction of the blood flow. Depending on the rigidity in bending of the cusps, the loss of their stability varies in nature. In one case the open cusps call for the back pressure differential in order to close while in another case the open cusps resist to the blood flow, this resistance being proportional to their rigidity in bending. A disadvantage of these constructions lies also in that the synthetic materials used for their preparation are not athrombogenic and result in formation of thrombin on the prosthesis.

Besides, in the course of cyclic operation of the prosthesis a rupture zone is apt to appear at the edges of the low stability zone which causes premature wear of the valve cusps.

Known in the prior art is a cardiac valve prosthesis (cf. U.S. Pat. No. 3,744,060, Cl. A61F 1/22, 1973) consisting of a tubular valve body with sinus-like bulges in its wall so that its external shape is pseudo dolioform (pseudo barrel shaped) and contains a number of thin resilient impermeable cusps. Each of said cusps interacts with the inner hollow formed by each bulge. The body and the cusps are made of an artificial material and the body is provided on the outside with a ring intended for suturing the valve to the heart.

The valve functions as follows. When pressure rises in the opening valve, the pliant cusps lose their stability. They move towards the corresponding hollows formed by sinus-like bulges, thus affording free passage for the blood flow. The upper edges of sinus-like bulges conduce to formation of circular vortices in said bulges after the cusps. Pressure in the circular vortices opposes the pressure of the blood flow which tends to press the cusps against the internal surface of the sinus-like bulges. As the flow decelerates, the cusps acted upon by the pressure of the circular vortices move inwardly so that their edges get in tight contact under the effect of back pressure differential.

Apart from the disadvantages inherent in all the artificial petal-type heart valve prostheses, the above-described construction is also deficient in an irregular conjugation of the cusps with the sinus-like bulges adjoining each other at an acute angle along the line of attachment. This brings about the formation of congested zones in the corners in the course of vortex-type flow of blood in the spaces after the cusps, the valves being open or closed. The shape-sustaining cusps, i.e. those possessing rigidity in bending, lose their stability when the valve is opened and move either to the open or closed position by flapping. This character of opening and closing of the cusps featuring rigidity in bending calls for an additional pressure differential on the valve. Besides, in view of the design features of the valve, the cusps and sinus-like bulges have different rigidity. Taking in account the absence of smooth conjugation of these elements, this brings about high shear stresses in the cusps along the line of attachment to the sinus-like bulges which also affects adversely the strength of the valve.

The currently used bioprosthetic heart valves, i.e. the prostheses made from an aortic valve of an animal or from a flap of biological tissue, while being not inferior in respect of hydraulic characteristics to the artificial prostheses, have an optimum central flow of blood and, what is most important, are thromboresistant, cause no hemolysis and do not call for life-long anticoagulant therapy. However, the problems of stepping up their reliability and durability are not yet solved and their hydraulic characteristics are still far from the natural prototypes, natural cardiac valves. The bioprosthetic heart valves comprise the cusps of the biological transplant made from the aortic valve of an animal or from a flap of biological tissue, e.g. pericardium, and a frame consisting of a supporting ring with struts extending therefrom. The framework is sewn over with biologically insert materials and is provided with a collar for suturing the valve into the heart.

The bioprosthetic valve functions as follows. It opens when pressure rises at the convex side of the closed cusps. Acted upon by the pressure differential, the cusps open, taking the space between the axially-arranged struts. The valve closes under the effect of the back pressure differential and of the blood flow. The back flow of blood entrains the closed cusps and forces them to close. The cusps close tightly under the effect of back pressure differential.

Numerous examples of failure of bioprostheses in the near and remote postoperative periods as well as the results of their stand tests at high loading frequencies testify to their insufficient strength and durability. The cusps fail most frequently in the zone where the cusps are attached to the axially arranged struts. Another vulnerable zone is the base of the cusps at the supporting ring. The results of intraoperative hemodynamic investigations of such bioprostheses prove that their hydraulic characteristics are far from those of the natural valves. This is attributed to the fact that the cusps open under the effect of the pressure differential which moves them towards the opening position while their closing calls for the back flow of blood which entails back-streaming through the valve.

Known in the prior art is, for example, a bioprosthetic heart valve (U.S. Pat. No. 4,106,129 NPC Cl. 3/1.5, 1978) comprising a skeleton of a resilient material and consisting of a supporting ring with struts extending therefrom a covering of a biologically inert material attached to which are the cusps of the biological transplant.

A peculiar feature of said bioprosthesis lies in that the forces occurring in the closing valve cusps act on the flexible struts, forcing them to move radially towards the valve axis. As the prosthesis opens, the struts come back to the initial position due to their resilience, and move the transplant cusps attached to them.

Apart from the disadvantages inherent in all the prostheses of this type, the prototype is deficient in that the fibrous ring of its transplant sown to the internal surface of the frame supporting ring and containing a considerable portion of muscular tissue makes the hydraulic lumen of the valve considerably narrower which raises hydraulic resistance. Besides, the axially protruding struts of the frame in the case of the bioprosthesis implanted into the atrioventricular position have been known in a number of cases to cause erosion and even laceration of miocardium tissue.

The above-cited disadvantages of bioprosthetic heart valves should be attributed to the misconceived idea according to which the aortic valve is a purely hydraulic mechanism and its mechanics are considered exclusively from the standpoint of hydraulics. In this case the functioning of the valve is regarded as ejecting the blood which spreads apart the cusps and opens the valve. The vortex mechanism of the initial closing of the aortic valve cusps in these constructions does not serve any purpose through absence in it of sinuslike formations which conduce to creation of a circular vortex after the open cusps of the valve.

There are various known methods of preparation of bioprosthetic heart valves.

For example, the known method of preparing the prosthesis of the heart valve (patent U.S. Pat. No. 4,035,849 Cl. A61F 1/22, 1977) consists in dissecting the aorta root with the aortic valve from the heart of an animal and cutting out a biological transplant with cusps and fibrous ring therefrom followed by mechanical cleaning, preparation and stitching the biological transplant to the frame.

Among the disadvantages of said method there is the impossibility of accurate matching of the transplant with the supporting frame which is due to extensive variations in the dimensions of the aortic valve used for a transplant.

When the transplant of a bioprosthetic heart valve is made from a flap of biological tissue, various devices are widely used for shaping the cusps, trimming and fixing them to the supporting frame. However said devices are not suitable for shaping the envelopes shaped like aortic sinuses concurrently with the cusps, said envelopes being vital in promoting the reliability and durability of the bioprosthesis. Besides, in these devices it is difficult to control the process of suturing since the sutures are applied not to a planar surface but over a spatial line of a complex configuration following the cusp-to-frame attaching contour.

Known in the art is a device for preparing a biological transplant from a fragment of biological tissue (French Patent No. 2399832, Cl. A61F 1/22, 1979), comprising a matrix and a punch, interconnected with each other. A fragment of biological tissue is arranged between the matrix and punch, whose opposite walls have a three-cusp profile; then the protruding tissue is trimmed, and the shaped cusps are fixed along the line of their attachment.

In addition to the disadvantages common to all similar devices, the above-described construction fails to provide a possibility of strengthening the sutures that fix the cusps by using biologically inert spacers.

Another known method of preparation of a biological transplant from a flap of biological issue (patent FRG No. 2822 464, Cl.A61 F 1/22, 1978) consists in bending the flap to form two layers, shaping the transplant cusps on the device in a solution of glutaraldehyde and stitching the biological transplant along the cusps attachment contour.

In the cited method one of the bends of the biological tissue flap mates with the free edge of the transplant cusps. In combination with the cyclic nature of loading of cusps, this brings about their rapid wear and ruptures along the line of bend. Besides, stitching of the flat flap of biological tissue bent in two fails to produce the desired shape and dimensions of the envelopes modelling the cusps and aortic sinuses required for optimum performance of the bioprosthesis.

An object of the present invention consists in making a bioprosthetic heart valve, in providing a method of making it from an aortic valve, a method and device for making it from a flap of biological tissue which should impart to said prosthesis the mechanical and biological characteristics closest to those of a natural aortic heart valve.

SUMMARY OF THE INVENTION

This object is achieved by providing a bioprosthetic heart valve comprising a frame made from a resilient material and consisting of a supporting ring with struts extending therefrom, with a covering from a biologically inert material used to attach the cusps of the biological transplant of the cardiac valve prosthesis in which, according to the invention, the frame is provided with an additional ring connected to the struts arranged on a toroidal plane while the frame covering forms a toroidal envelope isolated from inside with a layer of a material impermeable to ingrowth of the biological tissue, the biological transplant has envelopes shaped after aortic sinuses, secured to the supporting and additional rings while said cusps are fastened to said envelopes on a smooth mating plane, the number of envelopes corresponding to the number of cusps.

This brings the mechanical and biological characteristics of the bioprosthetic heart valve as close as possible to the performance characteristics of the natural aortic heart valve.

It is practicable that the arcuate portions of the supporting and additional frame rings be made as a continuation of the struts.

This will raise the mechanical reliability of and pliability the frame, and, in the long run, its damping role during valve operation, i.e. will promote the mechanical strength of the bioprosthetic heart valve as a whole.

The object is also achieved by providing a method of preparation of a biological transplant from an aortic valve for the bioprosthetic heart valve consisting in dissection the aortic root with the aortic valve from the heart of an animal or human being and cutting therefrom a biological transplant with cusps and fibrous ring with subsequent mechanical cleaning and preparation in which, according to the invention the biological transplant is cut out from the aortic root of an animal or human being along the upper edge of aortic sinuses, then the opening of the left coronary artery of the coronary sinus is sutured-in and the right corodary sinus is dissected along the lower edge of the right coronary artery.

This permits all the elements of the natural structure of the aortic valve to be completely used in the bioprosthetic heart valve which produces the hydraulic characteristics of the bioprosthesis approaching closely those of the natural aortic valve while the natural combination of the biological transplant element, i.e. cusps and aortic sinuses possessing heterogeneous mechanical properties, ensures the mechanical strength of the cusps of the bioprosthetic heart valve. Suturing-in the opening of the coronary artery and dissection of the right coronary sinus along the lower edge of the coronary artery ensures hermetic sealing of the valve.

The biological transplant for the bioprosthetic heart valve can be made from the aortic valve of an animal or human being so that the first transplant cut out from the aortic root along the upper edge of aortic sinuses is dissected to remove the noncoronary sinus with the cusp, then another biological transplant is cut out of the aortic root along the upper edge of aortic sinuses, the right coronary sinus with the cusp is dissected and removed from said second transplant, suturing-in instead the dissected noncoronary sinus with the cusp of the first biological transplant, then the opening of the left coronary artery is sutured in.

This permits reducing the hydraulic resistance of the bioprosthetic heart valve by ablating the muscular part of the right coronary cusp from the valve lumen, at the same time retaining the natural geometric and mechanical conjugation of the cusp and sinus sutured-in instead of the removed cusp and sinus, thereby ensuring mechanical reliability of the bioprosthetic heart valve.

This object is achieved also by making the biological transplant for the bioprosthetic heart valve from a flap of biological tissue with the aid of a device comprising interconnected matrix plates and a punch wherein, according to the invention, the punch takes the form of a plate whose active side is provided with a number of oval projections both surfaces of which have bulges shaped like the cusps of the aortic valve with aortic sinuses, the bulges shaped like cusps having a cutout arranged parallel to the active side of the punch plate and the matrix consists of two plates one of which has cutouts corresponding to the punch bulges shaped like aortic sinuses and both plates have holes running along the contour of the cutouts so that on joining the matrix plates with the punch said cutouts form a clearance corresponding to the contour for attaching the transplant cusps to the envelopes shaped like aortic sinuses, the punch plate carrying a removable pin secured parallel to the active side of said plate.

This permits the biological tissue flap to be used for cutting out a biological transplant shaped like the development of the aortic root with a natural aortic valve dissected along one of the commissures.

This makes it possible to prepare a biological transplant of any desired size while retaining the interrelations of the basic geometric dimensions of the cusps and aortic sinuses of a natural aortic valve. The clearance between the matrix and the punch permits the biological transplant to be assembled on the device on a planar surface thus facilitating the technological process of assembling the biological transplant from a biological tissue flap.

The object is also attained in the method of preparation of a biological transplant for the bioprosthetic heart valve from a biological tissue flap with the aid of a device said method consisting in bending a flap of biological tissue to form two layers, shaping the transplant cusps with the aid of the device in a solution of glutaraldehyde and stitching the biological transplant along the cusp-attaching contour wherein, according to the invention, one half of the biological tissue flap folded in two is used to cover the punch bulges shaped like aortic valve cusps, while the other half of the same flap is used to cover the punch bulges shaped like aortic sinuses and the line of bend of said flap is placed on the pin, after which the matrix plates are secured at both sides to the punch, thus producing a transplant blank, then the transplant blank is stitched by a filiform suture along the cutout in the punch bulges shaped like cusps, the transplant blank is trimmed at the side of the cusps while at the side of the envelopes shaped like aortic sinuses the blank is trimmed along the upper edge of the corresponding punch bulges after which the matrix plates are removed and the pin is pulled out of the transplant blank and punch; now the blank of the biological transplant is removed from the punch and stitched along the side edge of the envelopes shaped like aortic sinuses, thus producing the biological transplant of the bioprosthetic heart valve.

This provides for making the three-dimensional structure of the biological transplant from a biological tissue flap performing all the cutting out and stitching operations, but the last one, on a planar surface which facilitates and simplifies the technology and raises the accuracy of preparation of the biological transplant whose geometric shapes and dimensions approach closely those of the aortic root with the aortic valve.

This latter permits reproduction of the hydraulic operating principles of a natural aortic valve in the bioprosthetic heart valve. The suturing of the cusps of the biological transplant from a biological tissue flap with the envelopes shaped like aortic sinuses made from the same biological tissue flap increases the strength of the biological transplant as compared with the direct attachment of the cusps made from a biological tissue flap to the covering and frame of the biological prosthesis. This improves the strength of the bioprosthetic heart valve as a whole.

In another possible method of making the biological transplant from a biological tissue flap the biological transplant is stitched along the cusp-attaching contour through at least one spacer made from a biologically inert material, said spacer is secured to the matrix plate by a thread passed through the holes in said plate, the spacer protruding from the cutout contour by the value of the clearance corresponding to the contour of attaching the cusps to the envelopes shaped like aortic sinuses after which the biological transplant blank is stitched along the clearance through the spacers and the thread fastening the spacer to the matrix plate is removed.

This rules out the possibility of cutting through the biological tissue with the suture thread both at the moment of assembling the biological transplant and during assembly of the biological valve prothesis and in operation i.e. it promotes the strength and reliability of the bioprosthetic heart valve.

This object is also achieved in the method of preparation of the bioprosthetic heart valve from a biological transplant consisting in stitching the biological transplant to the frame wherein, according to the invention, the upper edge of each envelope shaped like aortic sinus is stiched to two adjacent arcuate portions of the additional ring by two separate sutures, the transplant is secured to the covering between said arcuate portions by two additional sutures and the lower edge of the biological transplant is arranged above the supporting ring flush with its internal surface and sewn to the supporting ring by a continuous suture, stitching through all the layers of the frame covering.

This permits the frame to retain the requisite axial and radial movability of the additional ring during operation of the bioprosthetic heart valve which, in turn, permits the elements of the biological transplant to execute the same motions as those occurring during operation of the natural aortic valve. In this way it becomes possible to prepare a biological prosthesis whose mechanical performance characteristics approach most closely those of a natural aortic valve. Besides, the attachment of the lower edge of the biological transplant flush with the internal surface of the supporting ring enlarges its flow area thereby reducing its hydraulic resistance. Application of the fixing sutures to the transplant along the line of two circumferences formed by the lower and upper edges of the envelopes shaped like aortic sinuses on the supporting and additional rings of the frame eliminates concentration of stresses and deformations in the cusps of the biological prosthesis caused by the fixing sutures and simplifies the technology of assembling the prosthesis.

Another possible method of preparing the bioprosthetic heart valve from a biological transplant presupposes that, when the supporting ring of the frame is made from separate arcuate portions, the lower edge of each envelope shaped like aortic sinus is arranged to match with each arcuate portion and flush with the internal surface of the supporting ring and stitched to said arcuate portions by separate sutures while the transplant is secured to the frame covering by additional sutures between said arcuate portions of the supporting ring.

This method improves the axial and radial compliance of the covered frame with the biological transplant sewn thereto. When the biological transplant is made from a biological tissue flap, this compliance adds to the damping function of the frame which relieves the fixing sutures, reduces stresses on the cusps and, in the long run, promotes strength and hydraulic characteristics of the bioprosthetic heart valve, bringing them closer to the characteristics of the natural aortic valve.

Now the disclosed invention will be described in detail by way of examples with reference to the attached drawings.

The claimed bioprosthetic heart valve is based on a radically new concept of the nature and functioning of the aortic valve (the natural aortic valve is not shown in the drawings), consisting in that the action of the aortic valve is defined not only and not so much by the hydraulic effect on its cusps at difference phases of the heart cycle as by the internal forces, deformations and motions occurring during these phases of the heart cycle in the elements of the aortic root (V. Sagalevich, N. Zavalishin, S. Dzemeshkevich, A. Nenjukov "Motions and forces in elements of valve-aorta complex at diastole and systole" Mechanics of composite materials. 1985, No. 1, pp 114–123; V. Sagalevich, N. Zavalishin, A. Nenjukov, B. Konstantinov. S. Dzemeshkevich, A. Ivanov "Mechanics of aortal root valves at diastole and systole. Part I.A. diastole. Biomechanics (PRB), 1984, No. 15–16, pp 34–36).

The aortic valve is an intricate three-dimensional structure based around a resilient frame secured to which are cusps and damping elements, i.e. aortic sinuses. Owing to interaction of all the aortic root elements the valve cusps are acted upon by the forces and motions of the resilient frame. Variations in the relation of forces applied to said frame within the heart cycle results in motions of its elements, which ensure an optimum mechanical loading and movement of the valve cusps. The provision of hydraulic dampers and an optimum combination of the mechanical properties of the cusps with the elements of the natural frame to which they are attached, ensures a high mechanical strength and extends the life of the valve. The cusps of the aortic valve are opened at the initial stage not by the pressure differential but under the effect of motions of the natural resilient frame during the isovolumic phase of heart systole which precedes the sphygmic phase. At the moment when blood starts flowing through the valve, the free edges of the cusps acted upon by the commissures moving up along the valve axis and outwardly from said axis, are lifted and open. At this moment the cusps are not stressed and, since they do not have any rigidity in bending, they are forced open by the blood flow, offering no resistance to bending. Owing to the fact that the specific weight of the cusps approaches that of blood, the cusps do not offer any inertia resistance to the blood flow. The cusps are closed when the commissural cores move back at the end of the sphygmic phase. As a result of these motions the free edges of the cusps go down along the valve axis and their extension decreases. The unstressed cusps easily close under the effect of circular vortices in the aortic sinus spaces at a drop of pressure during the reduced ejection phase. This ensures absence of regurgitation of the natural aortic valve.

The provision of the natural resilient frame with aortic sinuses located thereon also makes for a high mechanical reliability of the natural valve. This is due to the fact that the rigidity of the commissural cores carrying the cusps is somewhat lower than that of the cusps proper. Therefore the commissural cores are subjected to the concentrated incrase of stresses and deformations in the cusps along the line of their attachment. In their turn, the aortic sinuses function as elements counterbalancing the points where the commissures are secured to the aortic wall and serve as a sort of hydraulic damper during instantaneous, i.e. impact loading of the valve cusps by the back flow. The mechanical strength and durability of the valve have a strong reliance upon the fact that, owing to a flexible interaction of all the elements at a systole, the cusps move to the beginning of opening and close virtually unstressed. Thus, they change their configuration and make insignificant motions at a systole without flapping as stressed envelopes do, but experiencing only membrane extension in all their zones while being both open and closed.

BRIEF DESCRIPTION OF THE DRAWINGS

Now the disclosed invention will be described in detail by way of examples with reference to the attached drawings in which.

Figure 1:
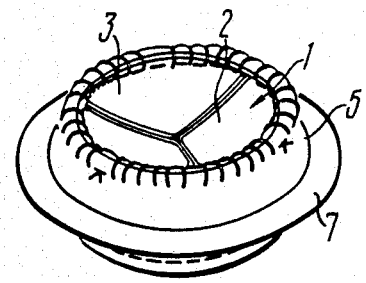
FIG. 1 is a general sectionalized axonometric view of the bioprosthetic heart valve according to the invention.
Figure 2:
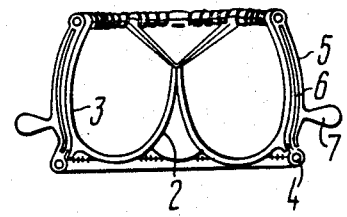
FIG. 2 is a general sectionalized view of the biological prosthesis according to the invention.

The claimed bioprosthetic heart valve comprises biological transplant 1 (FIG. 1) with cusps 2 and envelopes 3 shaped like aortic sinuses, frame 4 (FIG. 2), covering 5 with isolating spacer 6 and cuff 7.

Figure 3:
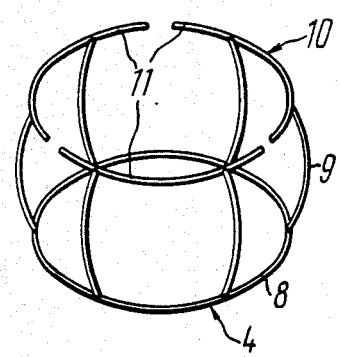
FIG. 3 is a general axonometric view of the frame of the bioprosthetic heart valve according to the invention.

Frame 4 (FIG. 3) consists of supporting ring 8, struts 9 extending from said ring over a toroidal surface and additional ring 10 joined with said struts 9 and consisting of separate arcuate portions 11. Frame 4 may be made, for example, of polypropylene or stainless wire.

Figure 4:
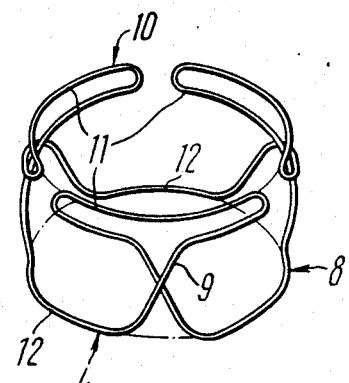
FIG. 4 is a general axonometric view of the frame of the biological prosthesis in which the arcuate portions of the additional and supporting rings are constituted by the continuation of struts.

Frame 4 (FIG. 4) of stainless wire is constructed so that additional 10 and supporting 8 rings are formed by the continuation of struts 9. In this case supporting ring 8 of frame 4, like additional ring 10 consists of separate arcuate portions 12.

Figure 5:
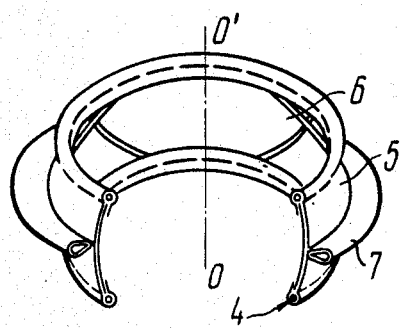
FIG. 5 is a general axonometric view of the covered-up frame of the biological prosthesis according to the invention.

Covering 5 (FIG. 5) of frame 4 is a toroidal envelope. Covering 5 made be made, for example, of knitted terylene. Adjoining the internal surface of covering 5 is an isolating spacer 6 which may be fabricated, for example, from finely-porous fluoroplastic material. The external surface of covering 5 carries cuff 7 which serves for fixing the bioprosthesis in the heart.

Figure 6:
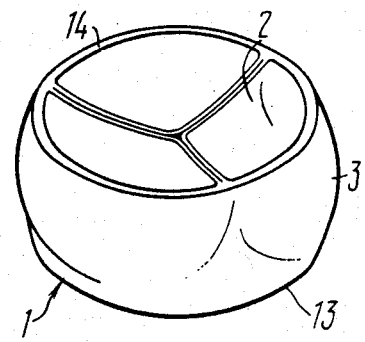
FIG. 6 is a general axonometric view of the biological transplant according to the invention.

As we have stated hereinbefore, biological transplant 1 (FIG. 6) comprises cusps 2 and smoothly mating envelopes 3 shaped like aortic sinuses, the lower 13 and upper 14 edges of transplant 1 being shaped in close resemblance of a circumference.

The above arrangement in the disclosed bioprosthesis ensures reproduction of the functional properties of the natural aortic heart valve, to wit, by using the damping and hydraulic functions of aortic sinuses; ensuring the motions of the bioprosthesis both in the radial and axial directions, duplicating the motions of the natural resilient frame of the aortic root, retaining its damping function and guaranteeing the natural closing of cusps 2. Besides, the structural peculiarities of the disclosed bioprosthesis ensure a reduction of the local stress concentrators along the attachment line of cusps 2 because transplant 1 is secured to frame 4 along two circumferences formed by lower 13 and upper 14 edges of transplant 1 and, correspondingly, supporting 8 and additional 10 rings of frame 4.

Figure 7:
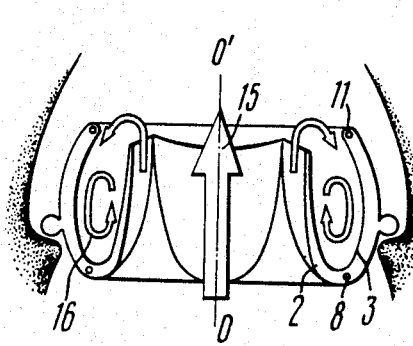
FIG. 7 is a schematic representation of the functioning of the bioprosthetic heart valve in the maximum blood flow phase according to the invention.

Schematically, the bioprosthetic heart valve has the following operating phases: at the moment of maximum straight blood flow 15 (FIG. 7) through the open bioprosthesis cusps 2 there exist closed vortices 16 after said cusps in the spaces formed by envelopes 3 shaped like aortic sinuses. Cusps 2 are in a state of dynamic equilibrium under the effect of equal pressures built up by flow 15 and vortices 16. At the same time, pressure of vortices 16 is transmitted to the walls of envelopes 3 shaped like aortic sinuses, which transmit forces to arcuate portions 11 of additional ring 10, forcing said portions to move mostly in a radial direction from axis 0—0' of the bioprosthesis. In its turn, this expands cusps 2, thus contributing to their maximum opening.

At the drop of the pressure differential which ensures the passage of the straight blood flow 15 through the bioprosthesis and during its deceleration, i.e. from the moment when a back pressure differential appears in straight flow 15, cusps 2 acted upon by vortices 16 move towards the axis 0—0' of the bioprosthesis. The space after them in envelopes 3 shaped like aortic sinuses increases and intensity of vortices 16 diminishes so that their action on the walls of envelopes 3 weakens and bioprosthesis frame 4 comes to its initial dimensions, i.e. arcuate portions 11 of additional ring 10 move radially towards the axis 0—0' of the bioprosthesis, thereby reducing the extension of cusps 2. The free edges of cusps 2 acted upon by subsiding vortices 16 continue their movement towards the axis 0—0' of the bioprosthesis up to the moment of their closure.

Figure 8:
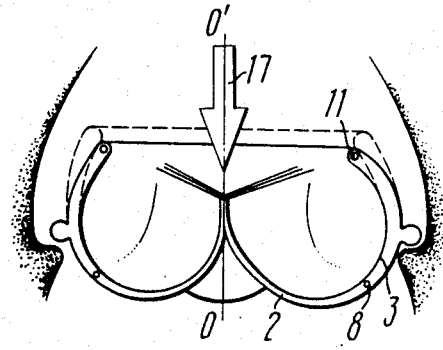
FIG. 8 is a schematic representation of the functioning of the bioprosthetic heart valve in maximum back pressure differential phase according to the invention.
Figure 11:
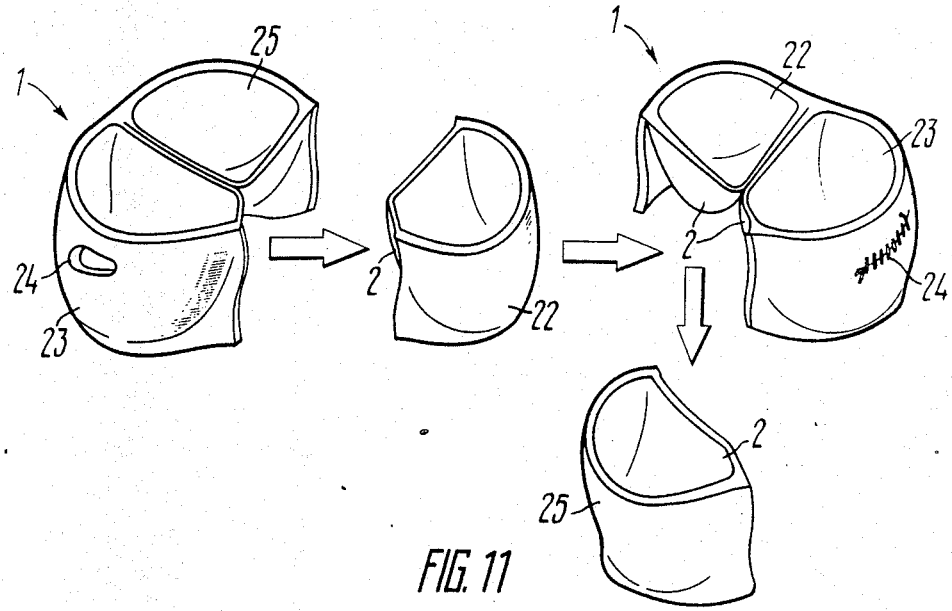
FIG. 11 shows schematically the preparation of the biological transplant from two aortic valves according to the invention.

Under the effect of the back pressure differential and the beginning back flow of blood 17 (FIG. 8) the free edges of cusps 2 close tightly. At this phase of the heart cycle there arises a pressure differential on cusps 2, caused by a faster reduction of pressure before the valve as compared with the pressure drop after the valve. Under the effect of the pressure differential certain forces arise in cusps 2 which are transmitted through envelopes 3 shaped like aortic sinuses onto arcuate portions 11 of additional ring 10. In proportion to the growing pressure differential on closed cusps 2 and to the change of pressure applied to envelopes 3 and in inverse proportion to rigidity of frame 4, arcuate portions 11 of additional ring 10 move axially towards supporting ring 8 and radially towards the axis of the bioprosthesis. Meanwhile the potential energy of deformation is being accumulated in frame 4. Curved struts 9 change the curvature of the toroidal surface of covering 5 and contribute to a change in the curvature of envelopes 3 shaped like aortic sinuses. This brings about redistribution of stresses in the walls of envelopes 3 which, together with deformation of frame 4, dampens the peak pressures caused by the hydraulic shock due to the disparity of the inertia of the cusps and of the adjoining blood column. Deformation of envelopes 3 also reduces the concentration of stresses in cusps 2 along their line of attachment.

As pressure rises before the bioprosthesis and, simultaneously, drops after it, the pressure differential on cusps 2 diminishes and so do the forces in the walls of envelopes 3. This sets free the potential energy in the deformed elements of frame 4 so that struts 9 unbend, moving arcuate portions 11 of additional ring 10 upward from supporting ring 8 and radially from the axis 0—0' of the bioprosthesis. Upper edge 14 of transplant 1 fixed in arcuate portions 11 of additional ring 10 moves in the same directions, pulling along envelopes 3 shaped like aortic sinuses, and cusps 2. The free edges of cusps 2 move upward along the axis 0—0' of the bioprosthesis and are extended.

When pressure is equalized on cusps 2, i.e. at a zero pressure differential, the forces in them diminish to zero and relieve completely the elements of frame 4 which recovers its initial dimensions.

The appearance of the positive pressure differential and the originating straight blood flow 15 through the bioprosthesis open cusps 2 which are unstressed and partly opened by the movements of frame 4. At upper edge 14 of transplant 1 part of the straight blood flow 15 gets separated and moves into the spaces formed by open cusps 2 and envelopes 3 shaped like aortic sinuses. In these spaces there arises vortices 16 which, owing to a smooth mating of cusps 2 and envelopes 3, flow over the inner spaces of transplant 1 without any congested and abruption zones. As the straight blood flow 15 reaches it maximum, the operating cycle of the biological prosthesis is repeated over again.

The method of preparation of biological transplant from the aortic valve for use in the biological prosthesis is realized as follows.

Figure 9:
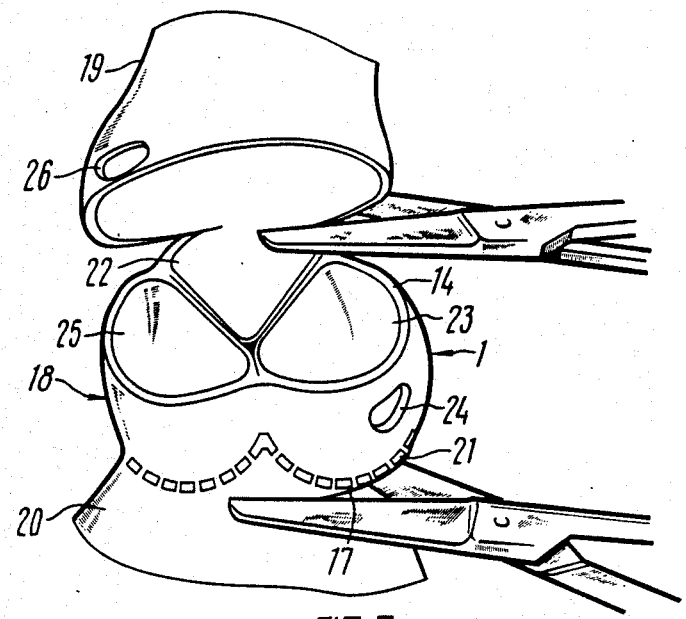
FIG. 9 shows the process of cutting out the biological transplant from the aortic root according to the invention.
Figure 10:
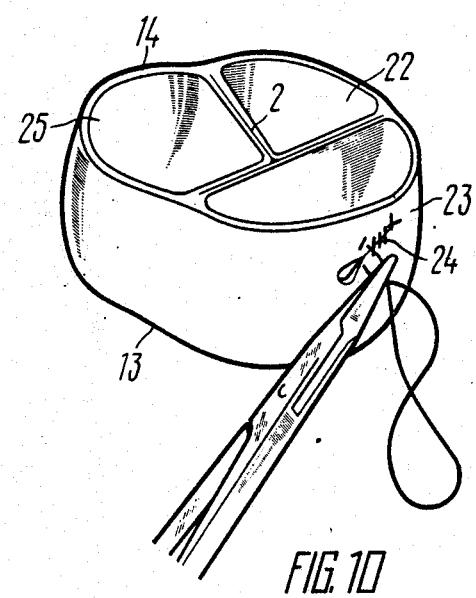
FIG. 10 shows the suturing-in of the opening of the left coronary artery of the biological transplant according to the invention.

Aortic root 18 (FIG. 9) of an animal or human being is taken with aortic arch 19 and a portion of myocardium 20 and transplant 1 is cut out therefrom along the lower edge of fibrous ring 21 which forms the lower edge 13 of transplant 1. Then aortic arch 19 is dissected over the upper edge of noncoronary sinus 22, along the upper edge of left coronary sinus 23 with left coronary artery 24 and along the right coronary sinus 25 through the lower edge of right coronary artery 26 thus forming upper edge 14 of transplant 1. Then the opening of left coronary artery 24 (FIG. 10) is sutured up.

Thus, transplant 1 is cut out over two surfaces located square to the axis of aortic root 18. This provides for simplicity and adaptability for industrial production of the claimed method for preparation of biological transplant 1 from the aortic valve for a biological prosthesis.

A realizable method of preparation of the biological transplant from the aortic valve for the bioprosthetic heart valve is put into practice as follows.

Noncoronary sinus 22 with cusp 2 is dissected from one biological transplant 1 (FIG. 1) then the right coronary sinus 25 with cusps 2 is dissected and removed from another biological transplant 1 and noncoronary sinus 22 with cusp 2 is sewn in the place from the first transplant 1. Then the opening of left coronary artery 24 is sewn up.

The advantages of the bioprosthesis made in keeping with the above method include an increase in the effective area of its opening and a reduced risk of clacification of the bioprosthetic heart valve due to absence of the muscular portion in the sewn-in noncoronary sinus 22 with cusp 2.

Figure 12:
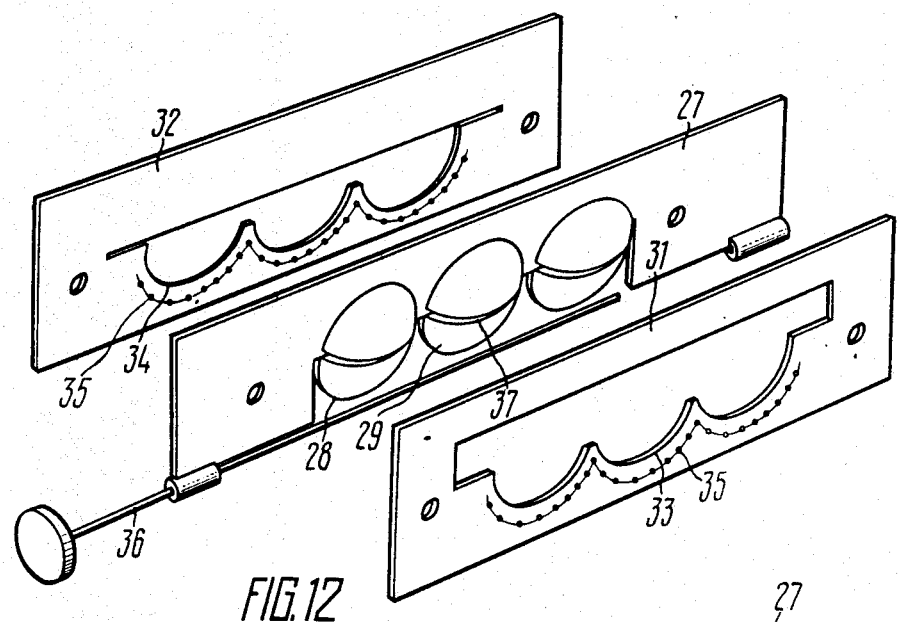
FIG. 12 shows the device for preparing the biological transplant from a flap of biological tissue according to the invention, axonometric view.
Figure 13:
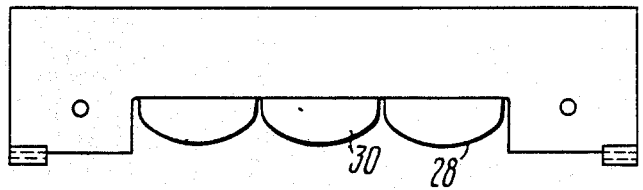
FIG. 13 shows the punch of the device for preparing the biological transplant from a flap of biological tissue at the side of the bulges shaped like aortic sinuses according to the invention, axonometric projection.

The device for the preparation of the biological transplant from a flap of biological tissue for the bioprosthetic heart valve comprises punch 27 (FIG. 12) with oval projections 28 along the edge which is its active side, bulges 29 shaped like the cusps of the aortic valve, and bulges 30 (FIG. 13) shaped like aortic sinuses located on the opposite surface of projections 28. The device also comprises a matrix in the form of two plates 31 and 32, plate 31 having cutout 33 corresponding to bulges 29 of punch 27, said bulges shaped like aortic valve cusps while plate 32 has cutout 34 corresponding to bulges 30 of punch 27, said bulges shaped like aortic sinuses. Plates 31 and 32 have holes 35 arranged along the contour of cutouts 33 and 34, punch 27 carries removable pin 36 while bulges 29 of punch 27 shaped like the aortic valve cusps have cutout 37, while removable pin 36 and cutout 37 are arranged parallel to the active side of punch 27.

This arrangement allows the claimed device to simultaneously form cusps 2 and envelopes 3 shaped like aortic sinuses from one flap of biological tissue. Besides, it ensures forming of the blank of transplant 1 in a developed state which facilitates considerably the stitiching and trimming of the blank of transplant 1 and thus improves the quality of said blank.

The method of preparing a biological transplant from a flap of biological tissue with the aid of the claimed device for making the biological transplant is realized as follows.

Figure 14:
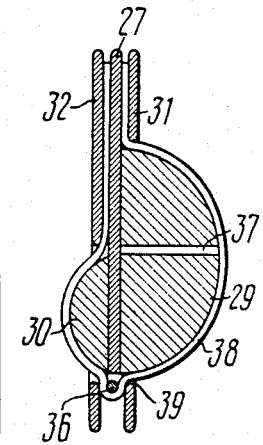
FIG. 14 is a cross-sectional view of the device for preparing the biological transplant with the transplant blank, according to the invention.
Figure 15:
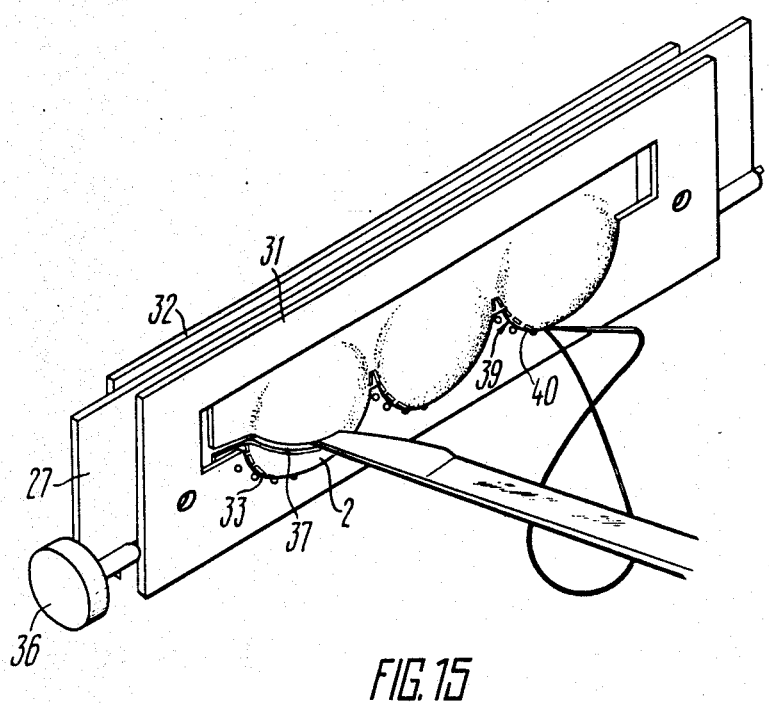
FIG. 15 shows the application of a filiform suture and trimming of the transplant blank on the claimed device at the side of the punch bulges shaped like cusps, according to the invention.

Biological tissue flap 38 (FIG. 14) is folded in two, and punch 27 with removable pin 36 attached to it is put into the folded flap 38 so that the line of bend of said flap 38 would pass along pin 36. Then plates 31 and 32 are secured on punch 27. The device with the blank of transplant 1 is immersed into a solution of glutaraldehyde or another tanning agent. On completion of tanning the device together with the blank of biological transplant 1 is withdrawn from the solution. Now a filiform suture 40 is applied along clearance 39 (FIG. 15) between cutouts 33 and 34 in plates 31 and 32 and oval projections 28 of punch 27, forming a development of the attaching line of cusps 2. The blank of transplant 1 is trimmed along cutout 37, forming the free edge of cusps 2 and the blank of transplant 1 is trimmed along the upper edge of bulges 30, forming the upper edge 14 of transplant 1. Plates 31 and 32, are removed, removable pin 36 and punch 27 are withdrawn from the blank of biological transplant 1. The biological transplant 1 is made from biological tissue flap 38 by stitching the blank of transplant 1 along the side edges of envelopes 3 shaped like aortic sinuses.

Another possible method of making a biological transplant from a biological tissue flap with the aid of the same claimed device for the preparation of the biological transplant can be realized as follows.

Figure 16:
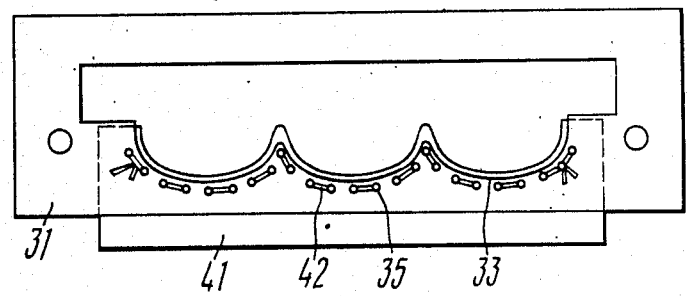
FIG. 16 shows the fastening of the spacer made from a biologically inert material to the matrix plate according to the invention.

Spacers 41 of biologically inert material, e.g. terylene velour are fastened to plates 31 (FIG. 16) and 32 with thread 42 passed through holes 35. Spacers 41 should be arranged on plates 31 and 32 so that they would protrude beyond the edges of cutouts 33 and 34 to the size of clearance 39 formed between cutouts 33, 34 and oval projections 28 of punch 27. Then plates 31 and 32 with spacers 41 are secured on punch 27. After tanning the elements, the blank of biological transplant 1 is stitched along clearance 39 through spacers 41 and thread 42 is pulled out.

This curtails the risk of through cutting of suture 40 along the attaching line of cusps 2, improves the quality of said suture and facilitates inprocess control of its application.

The method of preparation of a bioprosthetic heart valve is realized as follows. Frame 4 is wrapped along the external side surface by isolating spacer 6 and said spacer is fastened by a separate suture to the additional and supporting rings of the frame. Covering 5 is put on the frame with isolating spacer 6 and the upper edge of said covering is turned around arcuate portions 11 of additional ring 10 then stitched to covering 5 through isolating spacer 6. The lower edge of covering 5 is turned around supporting ring 8 and sewn to covering 5 through spacer 6.

Figure 17:
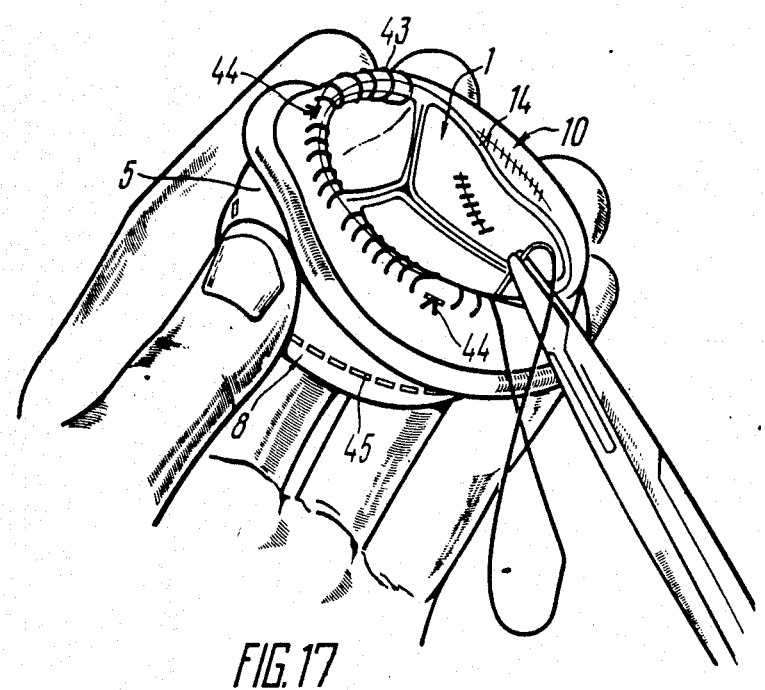
FIG. 17 is a schematic view of assembling the biological transplant on a covered frame during preparation of the bioprosthetic heart valve according to the invention.

Transplant 1 is sewn to additional ring 10 through upper edge 14 (FIG. 17) so that the upper edge of each envelope 3 shaped like aortic sinus is sewn to two adjacent arcuate portions 11 of additional ring 10 by two separate sutures 43. Between arcuate portions 11 the transplant 1 is secured to covering 5 by additional sutures 44. Lower edge 13 of transplant 1 is placed above supporting ring 8 of frame 4 flush with its internal surface then it is sewn to supporting ring 8 through all the layers of covering 5 and spacer 6 by continuous suture 45.

The above method of preparing the biological prosthesis does not call for careful matching and fitting of biological transplant 1 to frame 4 which promotes adaptability of said method for largescale production. Simultaneously, the total length of sutures 43, 44 and 45 securing transplant 1 to frame 4 diminishes as compared with currently existing methods thus increasing the reliability of the bioprosthesis prepared in keeping with the claimed method.

Figure 18:
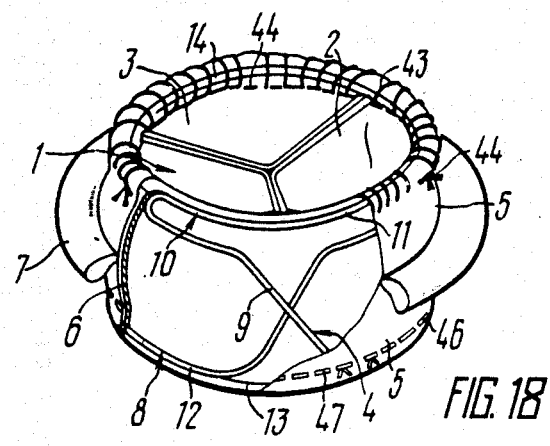
FIG. 18 shows schematically the process of assembling the biological transplant from a biological tissue flap stitched through the spacer on the covered-up frame whose supporting ring is made up of separate arcuate portions according to the invention.

Another possible method of preparing the bioprosthetic heart valve uses frame 4 whose supporting ring 8 is made up of separate arcuate portions 12. In this case the lower edge of covering 5 is wrapped around separate arcuate portions 12 of supporting ring 8 and sewn to covering 5, stitching through spacer 6. Lower edge 13 (FIG. 18) of transplant 1 is sewn to supporting ring 8 in such a manner that the lower edge of each envelope shaped like aortic sinus is installed corresponding to each arcuate portion 12 of supporting ring 8 flush with the internal surface thereof. In this case lower edge 13 of transplant 1 is sewn to arcuate portions 12 by separate sutures 46 while between the arcuate portions it is sewn by additional sutures, stitching through all the layers of frame covering 5.

This method imparts higher movability to supporting ring 8 of frame 4 thereby curtailing the concentration of stresses and deformations along the line of attachment of biological transplant 1. This proves most essential for transplant 1 prepared from biological tissue flap 38 which has no inextensible fibrous ring 21 along lower edge 13 as is the case with transplant 1 made from the aortic valve.

Up to the present time, the surgeons of the All-Union Scientific Surgical Centre of the USSR Academy of Sciences and of other cardiosurgical centres of the Sovient Union have made over 350 operations with the use of the claimed bioprosthesis. Not a single patient within a remote period up to 7 years has been suffering from dysfunction of bioprostheses caused by spontaneous collagenic degeneration. A statistical analysis by the method of actuarial curves demonstrates that 83.2% of patients have a chance to survive for as long as 5 years after the operation (taking in account the hospital lethality) without complications and at a minimum medicamentous therapy. If we come to estimate the survival rate taking heed of those reasons only which are related to bioprostheses alone, it will amount to 94%. If before operation all the patients belonged to the third and mostly fourth functional class according to the classification of the New-York Association of Cardiologists, after the operation in the remote period 81.3% of the patients were put into the first and second classes and only 18.7% to the third, fourth classes. The mean functional class calculated for the entire group of the operated-on patients, was 3.86% while for the patients supervised after the operation it came only to 2.17.

What is claimed is:

1. A bioprosthetic heart valve comprising:
a frame of a resilient material with a circular base; struts joined to said base and arranged over a toroidal surface; an additional ring arranged axially with relation to said circular base and made up of separate arcuate portions joined to said struts;
an isolating spacer made from a biologically inert material, impermeable to in growth of biological tissues, fitting around the external surface of said frame and replicating its toroidal shape;
a covering of a biologically inert material fitting around the external surface of said frame, replicating its toroidal shape and arranged directly on top of said isolating spacer;
threads passing through sid covering and spacer and stitching them to said frame;
a biological transplant made from the aortic root of an animal or human being and having a left coronary sinus with a cusp, a right coronary sinus with a cusp, a noncoronary sinus with a cusp and a fibrous ring; the upper edge of said sinuses is secured to said additional ring and said covering so that the upper edge of each of said sinuses is located on said adjacent arcuate portions of said additional ring; the lower edge of said biological transplant is secured on said covering above said circular base;
threads passing through said biological transplant and stitching it to said rings and said covering.

2. A bioprosthetic heart valve comprising:
a frame of a resilient material with a circular base consisting of separate arcuate portions; struts being a continuation of said arcuate portions and arranged over a toroidal surface; an additional ring arranged axially with relation to said circular base, consisting of separate arcuate portions which are a continuation of said struts;
an isolating spacer of a biologically inert material, impermeable to in growth of biological tissue, fitting around the external surface of said frame and replicating its toroidal shape;
a covering of a biologically inert material, fitting around the external surface of said frame, replicating its toroidal shape and located directly on top of said isolating spacer;
threads passing through said covering and spacer and stitching them to said frame;
a biological transplant made from a flap of biological tissue and having at least three sinus-like envelopes shaped like the aortic sinuses of the aortic heart vale, and cusps whose number corresponds to the number of said sinus-like envelopes, attached to said sinus-like envelopes and joining them smoothly; the upper edge of said biological transplant is secured on said additional ring and said covering so that the upper edge of each of said sinus-like envelope is located on said adjacennt arcuate portions of said additional ring; the lower edge of said biological transplant is secured to said covering above said arcuate portions of the circular base;
threads passing through said biological transplant and stitching it to said rings and covering.

3. A method of preparing a biological transplant for the bioprosthetic valve as claimed in claim 1 from the aortic root of an animal or human being with the aortic valve having the left coronary sinus with the opening of the left coronary artery and cusp; the right coronary sinus with the opening of the right coronary artery and cusp; the noncoronary sinus with a cusp; a fibrous ring and the remainder of the muscular tissue comprising:
cutting out a blank of the biological transplant from said aortic root complete with said cusps and aortic sinuses along the lower edge of said fibrous ring, along the upper edge of said left coronary sinus, then along the upper edge of said noncoronary sinus, then along the upper edge of said noncoronary sinus and along said right coronary sinus through said opening of the right coronary artery;
cleaning of said biological transplant blank of said remainder of muscular tissue;
suturing-in said opening of the left coronary artery of said left coronary sinus, thus producing a biological transplant for the bioprosthetic heart valve.

4. A method of preparing the biological transplant for the bioprosthetic heart valve as claimed in claim 1 from at least two (first and second) aortic roots of an animal or human being with aortic valves having, each, the left coronary sinus with the opening of the left coronary artery and a cusp, the right coronary sinus with the opening of the right coronary artery and a cusp; the noncoronary sinus with a cusp, a fibrous ring and the remainder of the muscular tissue, comprising:

cutting out the first blank of the biological transplant from said frist aortic root with said cusps and aortic sinuses along the lower edge of said fibrous ring, along the upper edge of said left coronary sinus, then along the upper edge of said non-coronary sinus and along said right coronary sinus through said opening of the right coronary artery;

cutting out a second biological transplant blank complete with said cusps and aortic sinuses from said second aortic root along the lower edge of said fibrous ring, along the upper edge of said left coronary sinus then along the upper edge of said non-coronary sinus and said right coronary sinus through said opening of the right coronary artery;

cleaning of both of said blanks of the biological transplants from said remainder of muscular tissue;

dissecting said noncoronary sinus with the cusp from said first blank of the biological transplant;

stitching in said dissected noncoronary sinus with the cusp from said first blank of the biological transplant in place of said right coronary sinus with the cusp from said second blank of the biological transplant;

suturing in said opening of the left coronary artery of said left coronary sinus of said second blank of the biological transplant thereby producing the biological transplant for the bioprosthetic heart valve.

5. A device for preparing the biological transplant from a flap of biological tissue for the bioprosthetic heart valve as claimed in claim 2 comprising:

a punch made in the form of a plate with four edges one of which having a number of oval projections configured like a development of the attaching line of said cusps to said aortic sinuses; a row of bulges arranged on one side of said projections replicating the cusps of said biological transplant; another row of bulges arranged on the other side of said projections replicating the sinus-like envelopes of said biological transplant; said bulges on the opposite sides of each of said projections are smoothly mating with each other; a slot located on said bulges shaped like cusps and passing parallel to the line tangent to the apices of said projections;

a matrix in the form of two plates; said plates have cutouts in the centre whose configuration corresponds to the contour of said bulges of said punch; said cutouts jointly with said oval projections form a clearance for stitching;

a removable pin secured on said punch and arranged parallel to said tangent to the apices of said projections and at a certain distance from them, the width of this distance corresponding to the width of said stitching clearance.

6. A device claimed in claim 5 in which, in case of the provision of a reinforcing spacer, said plates of said matrix have a row of holes arranged along the contour of said cutouts and intended for fixing the reinforcing spacer.

7. A method for preparing the biological transplant from a flap of biological tissue using the device of claim 5 comprising:

applying the biological tissue flap to one side of said punch followed by turning it over on the other side of said punch so that the thus formed line of bend of said biological tissue flap is arranged on said removable pin and both halves of said biological tissue flap are used to cover said bulges on both sides of said oval projections;

applying said matrix plates on both sides of said punch on top of said biological tissue flap so that said bulges on said oval projections of said punch enter into said cutouts on said matrix plates and form said stitching clearance, and subsequent fixing of said matrix plates on the punch;

applying a filiform suture along said clearance which forms the cusp-attaching contour thus producing the blank of the biological transplant;

trimming said blank of the biological transplant along said slot in said bulges shaped like cusps thus forming the free edge of said cusps;

trimming the upper edge of said bulges shaped like said sinus-like envelopes of said biological transplant blank, thus forming the upper edge of said sinus-like envelopes;

removing said matrix plates from said punch;

pulling said removable pin from said punch and said blank of the biological transplant;

removing said blank of the biological transplant from said punch;

coiling said blank of the biological transplant into a tube and stitching it along the side edges of said sinus-like envelopes, thus producing said biological transplant for the bioprosthetic heart valve.

8. A method of preparation of the biological transplant from a flap of biological tissue using the device of claim 6 comprising:

applying the flap of biological tissue to one side of said punch and turning it over to the other side of said punch, arranging the line of bend of said flap on said removable pin and covering said bulges on both sides of said oval projections completely with both halves of said flap of biological tissue;

applying a reinforcing spacer made from biologically inert material to at least one of said matrix plates at the side facing said flap of biological tissue and fixing it on said matrix plate with a thread passed through said holes located along the contour of said cutout of said plate, said reinforcing spacer protruding beyond the contour of said cutout to a distance equal to said stitching clearance;

applying said matrix plates with said reinforcing spacer to said punch on both sides on top of said flap of biological tissue so that said bulges on said oval projections of said punch do not enter into said cutouts of said matrix plates and form said clearance for stitching with subseauent fixing of said matrix plates on said punch;

applying a filiform suture along said clearance for stitching, sewing through said reinforcing spacer, said suture forming the attaching contour of said cusps, thereby producing said blank of the biological transplant;

removing said thread which fixes said spacer to said matrix plate;

trimming said blank of biological transplant along said slot in said bulges shaped like said cusps, thus forming the free edge of said cusps;

trimming said blank of biological transplant along the upper edge of said bulges shaped like sinus-like envelopes, thus forming the upper edge of said sinus-like envelopes;

removing said matrix plates from said punch;

pulling out said removable pin from said punch and said blank of biological transplant;

removing said blank of biological transplant from said punch;

coiling said blank of biological transplant into a tube and stitching it up along the side edges of said sinus-like envelopes, sewing up said reinforcing spacer and thus producing the biological transplant for the bioprosthetic heart valve.

9. A method of preparation of the bioprosthetic heart valve according to claim 1 from the biological transplant made from the aortic root with the aortic valve of an animal or human being and having the left coronary sinus with the cusp, the right coronary sinus with the cusp, the noncoronary sinus with the cusp and the fibrous ring comprising:

wrapping said frame over the external side surface with said isolating spacer and fixing it by separate filiform sutures to said rings of the frame;

slipping said covering on said frame on top of the isolating spacer, said covering having the upper and lower edges; turning said upper edge of said covering around said arcuate portions of said additional ring and stitching it to said covering, through said isolating spacer; turning said lower edge of said covering around said circular base and sewing it to said covering, through said isolating spacer;

placing said biological transplant into said frame with each of said sinuses arranged directly on two adjacent arcuate portions of said additional ring;

sewing the upper edge of each of said sinuses to said two arcuate portions of said additional ring by two separate sutures;

sewing said upper edge of said biological transplant to said covering between said arcuate portions of said additional ring by additional sutures;

sewing said lower edge of said biological transplant to said covering through said isolating spacer above said circular base.

10. A method of preparing the bioprosthetic heart vavle according to claim 2 from the biological transplant made from a flap of biological tissue and having at least three sinus-like envelopes shaped after the aortic sinuses, and cusps whose number corresponds to the number of said sinus-like envelopes, attached to said envelopes and smoothly joined to them comprising:

wrapping said frame over the external side surface with said isolating spacer and fastening it with separate filiform sutures to said frame rings;

slipping said covering having the upper and lower edges on said frame on top of the isolating spacer; turning said upper edge of the covering around said arcuate portions of the additional ring and sewing it to said covering through said isolating spacer; then turning said lower edge of the covering around said arcuate portions of said circular base and sewing it to said covering, stitching through said isolating spacer;

placing said biological transplant into said frame so that each sinus-like envelope is arranged on two adjacent arcuate portions of said additional ring and above each said arcuate portion of the circular base;

sewing the upper edge of each said sinus-like envelope to said two adjacent arcuate portions of said additional ring by two separate sutures;

sewing said upper edge of said biological transplant to said covering between said arcuate portions of said additional ring by additional sutures;

sewing said lower edge of said biological transplant through the isolating spacer above the arcuate portions of the circular base;

sewing said lower edge of said biological transplant between said arcuate portions of the circular base to said covering through said isolating spacer by additional sutures.

11. The method of preparing the bioprosthetic heart valve according to claim 10 wherein said lower edge of said reinforcing spacer is turned out onto said covering and sewn to the latter.

* * * * *